United States Patent
Chen et al.

(10) Patent No.: US 11,939,528 B2
(45) Date of Patent: Mar. 26, 2024

(54) METHOD FOR PREPARING BIOCHAR AND HYDROGEN BY UTILIZING ANAEROBIC FERMENTATION BYPRODUCTS

(71) Applicant: TIANJIN UNIVERSITY, Tianjin (CN)

(72) Inventors: Guanyi Chen, Tianjin (CN); Xiang Guo, Tianjin (CN); Yurou Mao, Tianjin (CN); Beibei Yan, Tianjin (CN); Yanbin Zhang, Tianjin (CN); Junyu Tao, Tianjin (CN); Wanqing Li, Tianjin (CN); Zhanjun Cheng, Tianjin (CN); Wenchao Ma, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 338 days.

(21) Appl. No.: 17/298,137

(22) PCT Filed: Oct. 16, 2019

(86) PCT No.: PCT/CN2019/111508
§ 371 (c)(1),
(2) Date: May 28, 2021

(87) PCT Pub. No.: WO2021/072684
PCT Pub. Date: Apr. 22, 2021

(65) Prior Publication Data
US 2022/0017825 A1 Jan. 20, 2022

(51) Int. Cl.
*C10B 57/10* (2006.01)
*B01J 23/10* (2006.01)
(Continued)

(52) U.S. Cl.
CPC .............. *C10B 57/10* (2013.01); *B01J 23/10* (2013.01); *B01J 23/755* (2013.01); *B01J 37/08* (2013.01);
(Continued)

(58) Field of Classification Search
CPC ......... C10B 57/10; C10B 47/02; C10B 57/16; C10B 53/02; B01J 23/10; B01J 23/755;
(Continued)

(56) References Cited

U.S. PATENT DOCUMENTS 11,168,339 B1 * 11/2021 Stepany ................. C12P 5/023
2013/0330797 A1 * 12/2013 Olsen ..................... C12P 19/02
435/167

(Continued)

FOREIGN PATENT DOCUMENTS

CN 102337302 2/2012
CN 107986233 5/2018
(Continued)

OTHER PUBLICATIONS

International Search Report and Written Opinion issued in corresponding PCT Patent Application No. PCT/CN2019/111508, dated Apr. 22, 2020.

*Primary Examiner* — Ellen M McAvoy
(74) *Attorney, Agent, or Firm* — Pillsbury Winthrop Shaw Pittman, LLP (57) ABSTRACT

A method for preparing biochar and hydrogen by utilizing anaerobic fermentation byproducts, the method including: (1) mixing a first straw, seeding sludge and distilled water, and then carrying out anaerobic fermentation to obtain a mixed product after fermentation; (2) performing separation on the mixed product to obtain a second straw and biogas slurry; and (3) carbonizing the second straw to obtain biochar, and collecting gas after a pressurized catalytic reaction on the biogas slurry to obtain hydrogen.

15 Claims, 6 Drawing Sheets

(51) Int. Cl.
  *B01J 23/755* (2006.01)
  *B01J 37/08* (2006.01)
  *C01B 3/40* (2006.01)
  *C10B 47/02* (2006.01)
  *C10B 57/16* (2006.01)
  *C12P 3/00* (2006.01)

(52) U.S. Cl.
  CPC .............. *C01B 3/40* (2013.01); *C10B 47/02* (2013.01); *C10B 57/16* (2013.01); *C12P 3/00* (2013.01); *C01B 2203/1628* (2013.01); *C12P 2203/00* (2013.01)

(58) Field of Classification Search
  CPC ... B01J 37/08; B01J 37/18; B01J 21/04; B01J 23/83; C01B 3/40; C01B 2203/1628; C01B 2203/0233; C01B 2203/1058; C01B 2203/1082; C01B 32/05; C12P 3/00; C12P 2203/00; C12P 5/023; C01P 2006/12; Y02E 50/10; Y02E 50/30; Y02P 20/52

See application file for complete search history.

(56) References Cited

U.S. PATENT DOCUMENTS

| | | | |
|---|---|---|---|
| 2014/0186929 A1* | 7/2014 | Davis | C12P 5/023 435/252.4 |
| 2016/0153008 A1* | 6/2016 | Josse | C10B 53/02 435/167 |
| 2022/0290065 A1* | 9/2022 | Haddad | C10L 9/086 |

FOREIGN PATENT DOCUMENTS

| | | |
|---|---|---|
| CN | 108504696 | 9/2018 |
| CN | 110002445 | 7/2019 |

* cited by examiner

METHOD FOR PREPARING BIOCHAR AND HYDROGEN BY UTILIZING ANAEROBIC FERMENTATION BYPRODUCTS

This application is the U.S. national phase entry of PCT Patent Application No. PCT/CN2019/111508, filed Oct. 16, 2019.

TECHNICAL FIELD

The present disclosure relates to the resource utilization, energy utilization and environmental fields of byproducts during the energy conversion process, and more specifically to a method for preparing biochar and hydrogen by utilizing anaerobic fermentation byproducts.

BACKGROUND ART

By the end of 2014, the number of household biogas digesters in China had reached 41.50 million, with an annual biogas output of 13.67 billion $m^3$; the number of intensive biogas projects was 99,957, with an annual biogas output of 2.103 billion $m^3$. It is estimated that, by the end of "the 13th Five-Year Plan", the number of biogas projects will reach 139,295, with an annual biogas output of 44 billion $m^3$. According to the literature data, for a biogas project with a power of 500 kW, the annual output of fermentation byproducts (biogas residue and biogas slurry) is up to 10,000 tons (with the water content of approximately 90%). The output of anaerobic fermentation byproducts (biogas residue and biogas slurry) is huge, and their resource recycling utilization has become a bottleneck restricting the popularization and application of anaerobic fermentation technology.

The anaerobic fermentation byproducts are rich in the nutrient element nitrogen, and currently often used as bio-organic fertilizers to replace part of chemical fertilizers, while there is a risk of soil nitrogen exceeding the standard for fertilizer use. In addition, in the fertilizer use of anaerobic fermentation byproducts, there are also risks of the pathogenic bacteria and heavy metal pollution, odor pollution, dioxin and polychlorobiphenyl pollution, etc. The anaerobic fermentation process using straw as the substrate converts only part of the cellulose and most of the hemicellulose, and there are a large residual amount of biogas residues. The biogas slurry is the residual liquid after anaerobic fermentation, and at present is mostly used as fertilizers and feed additives. However, the antibiotics and pathogenic microorganisms in the biogas slurry may cause potential harms to the environment and human health. The biogas slurry is rich in the nutrient element nitrogen and is often used as organic fertilizers. But its acceptability is not high, and the availability for farmers is only about 30%. In addition, the environmental and ecological risks for the use of biogas slurry fertilizers are not yet clear. The risks are occurred for open discharge from time to time, and it is easy to cause odor pollution and pollute the soil and groundwater. Therefore, the fertilizer use is not an effective way for disposal of the anaerobic fermentation byproducts, and new disposal ways are urgently needed to be developed.

Biochar is a carbon-rich solid product produced by high-temperature thermal cracking of biomass under anoxic or anaerobic conditions, and is called as "black gold" in the scientific community. Virtually the production of biochar is the thermal cracking process of lignin, cellulose and hemicellulose. During the pyrolysis, lignin is the main contributor to biochar due to the presence of aromatic rings in the structure with a mild reaction. Hemicellulose is almost completely converted into small molecular gas due to its amorphous structure and the presence of unstable branched chains. Cellulose is mainly transformed into organic volatiles (tar) and a small amount of biochar. Therefore, since the straw itself is rich in cellulose, it is inevitable that byproducts such as tar are produced during the carbonization, which block up the pores of biochar, resulting in a small specific surface area of biochar prepared by direct pyrolysis of straw, which affects the performance of straw biochar to some extent. Anaerobic fermentation can selectively degrade cellulose/hemicellulose that is easily converted into organic volatiles (tar) during the pyrolysis for biochar production, to reduce the generation of tar from the source, thereby reducing the risk of blocking the pores of biochar by the tar during carbonization. After fermentation, the structural disorder of the biomass lignocellulose increases, which can enhance the mass and heat transfer process during the carbonization, contributing to the rapid escape of volatiles and leaving abundant pores, thereby preparing the biochar with a high specific surface area. The anaerobic fermentation technology has developed to be mature and widely used in the production of bio-combustible gas. The use of solid byproducts after anaerobic fermentation treatment in the production of briquette fuel and bio-oil is still in the stage of laboratory research, and the fermentation temperature is demanding and the period is long. Currently, there is no report about the carbonization of solid byproducts after anaerobic fermentation treatment to produce biochar with a high specific surface area.

There are a large number of organic compounds such as polycyclic aromatic hydrocarbons, phenolic compounds, and phthalates, or the like in the biogas slurry. If they can be converted into fuel gas for use, it will be an ideal way to improve the comprehensive utilization rate of biogas slurry and alleviate the energy crisis. The current technology involving the research on hydrogen production from biogas slurry mainly includes the steam reforming technology. However, in this method, the steam reforming for hydrogen production technology vaporizes the biogas slurry at a high temperature (500-700° C.) and normal pressure before reforming to produce hydrogen, and is accompanied by side reactions that are easily occurred at a high temperature. This method requires relatively high process conditions, relatively complicated operations, and the reaction product contains a small amount of harmful gases, and the production cost is relatively high, which is difficult for industrial production and application. Therefore, it is necessary to investigate the direct one-step reaction for producing hydrogen under relatively mild reaction conditions to reduce the side reactions that are easily occurred under high temperature conditions.

SUMMARY OF INVENTION

One of the main objectives of the present disclosure is to propose a method for preparing biochar and hydrogen by utilizing anaerobic fermentation byproducts, as well as biochar prepared from biogas residues, in order to at least partially solve at least one of the above technical problems.

To achieve the above objective, as an aspect of the present disclosure, a method for preparing biochar and hydrogen by utilizing anaerobic fermentation byproducts is provided, which comprises:

mixing a first straw, seeding sludge, and distilled water for anaerobic fermentation to obtain a fermented mixed product;

separating the fermented straw from the mixed product to obtain a second straw; and separating and recovering a biogas slurry from the mixed product;

carbonizing the obtained second straw to obtain the biochar; and collecting the gas, i.e., the hydrogen, after a pressurized catalytic reaction of the obtained biogas slurry.

As another aspect of the present disclosure, the biochar prepared by the above method is also provided.

List of Reference numbers: 1—crucible, 2—the first high-temperature resistant ceramic pipe plug, 3—the second high-temperature resistant ceramic pipe plug, 4—stainless steel pushrod, 5—mass flowmeter, 6—high-temperature tube furnace, 7—temperature control system, 8—condenser, 9—filter, 10—pyrolytic gas purification system.

DESCRIPTION OF EMBODIMENTS

Figure 2:
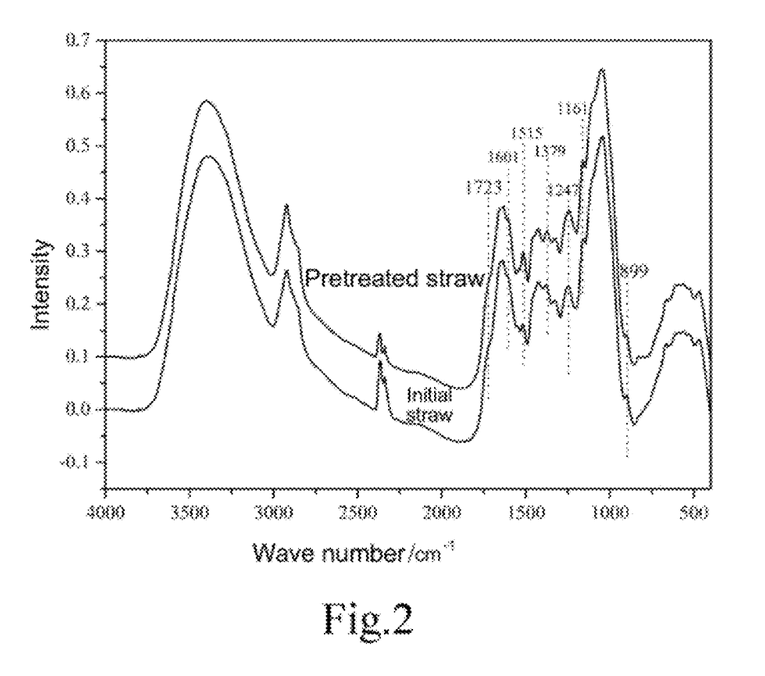
FIG. 2 is a Fourier transform infrared spectrum of the straw before and after the anaerobic fermentation treatment in Example 1 of the present disclosure.
Figure 3:
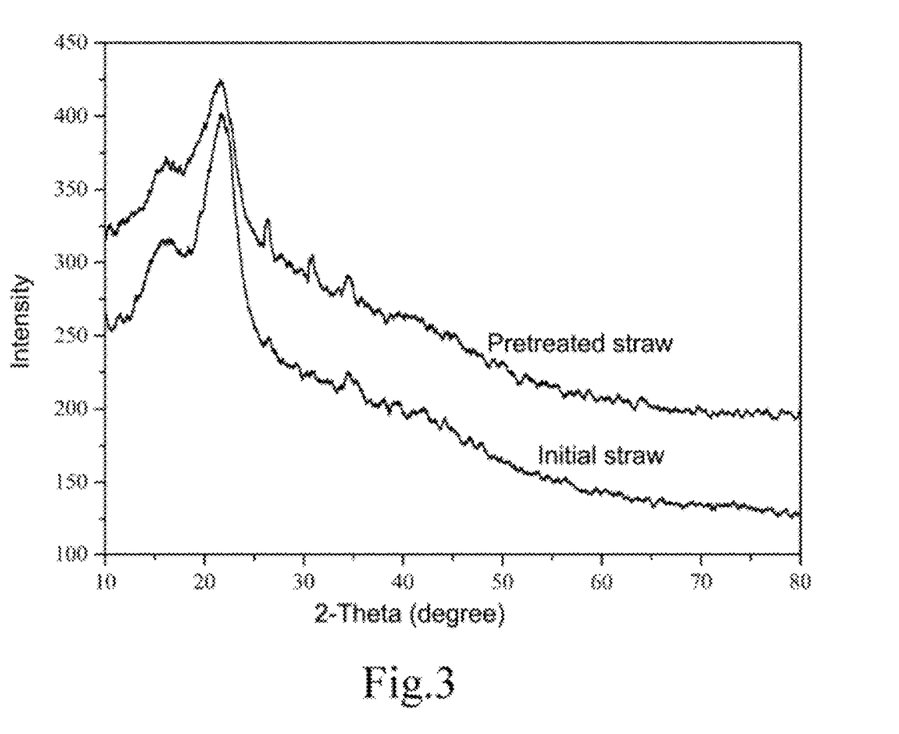
FIG. 3 is an X-ray diffraction pattern of the straw before and after the anaerobic fermentation treatment in Example 1 of the present disclosure.
Figure 4:
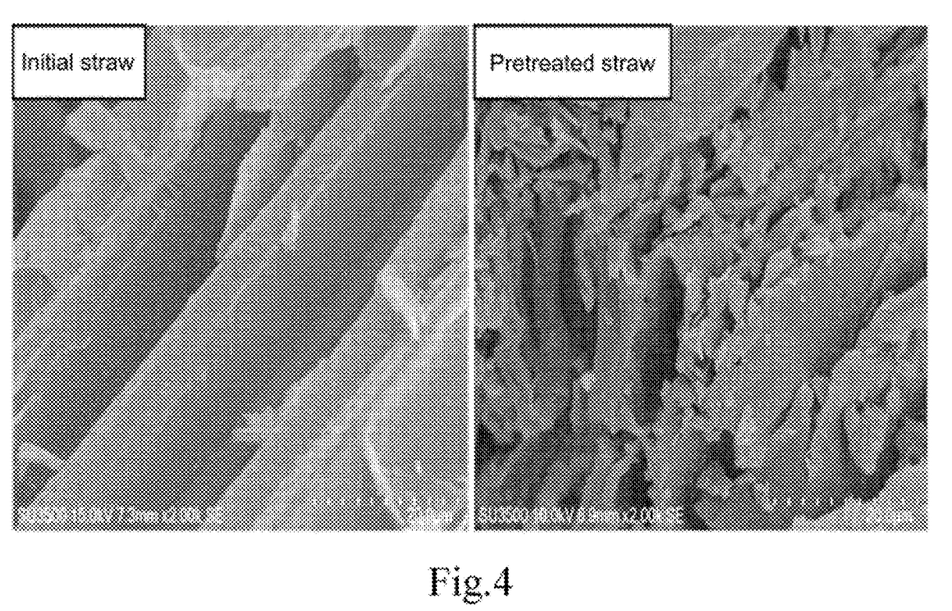
FIG. 4 is a scanning electron micrograph of the straw before and after the anaerobic fermentation treatment in Example 1 of the present disclosure.

The present disclosure discloses a method for preparing biochar and hydrogen by utilizing anaerobic fermentation byproducts, the method comprising:

mixing a first straw (also referred to as initial straw, as shown in FIG. 2, 3, 4, or a1, seeding sludge, and distilled water for anaerobic fermentation to obtain a fermented mixed product;

separating the fermented straw from the mixed product to obtain a second straw (also referred to as initial straw, as shown in FIG. 2, 3, 4, or 6); and separating and recovering a biogas slurry from the mixed product;

carbonizing the obtained second straw to obtain the biochar; and collecting the gas, i.e., the hydrogen, after a pressurized catalytic reaction of the obtained biogas slurry.

Preferably, the mass ratio of the seeding sludge to the first straw is (25-30):1.

Preferably, the mass ratio of the distilled water to the first straw is (10-20):1.

Preferably, the length of the first straw is 2-3 cm.

Preferably, the first straw is an air-dried straw.

Preferably, the second straw is washed and dried before the carbonization step.

Preferably, the mesh number of the second straw is 40-80 mesh.

Preferably, the anaerobic fermentation is realized in an anaerobic fermentation tank.

Preferably, the seeding sludge is a discharged sludge from the anaerobic fermentation tank.

Preferably, in the anaerobic fermentation step, the fermentation temperature is 20-25° C.; the fermentation time is 7-14 days; and the materials are stirred every 10-14 hours.

Preferably, during the anaerobic fermentation, the anaerobic environment is realized by introducing inert gases.

Preferably, the inert gas comprises nitrogen.

Preferably, the carbonization step is realized in a pyrolytic carbonization device.

Preferably, the pyrolytic carbonization device comprises a high-temperature tube furnace.

Preferably, in the carbonization step, the high-temperature tube furnace has a carbonization temperature of 750-850° C. and a pyrolytic carbonization time of 50-70 min.

The present disclosure also discloses the biochar prepared by the above method, characterized in that, the specific surface area of the biochar is 240-288 $m^2/g$.

Preferably, the step of collecting gas after a pressurized catalytic reaction of the obtained biogas slurry specifically comprises: after adding a catalyst to the biogas slurry, reacting under pressurized conditions, then cooling and collecting gas.

Preferably, the concentration of the catalyst is 2-5 g/L.

Preferably, the reaction pressure is 1.5-5.0 MPa, more preferably 2.5-3.0 MPa.

Preferably, the reaction temperature is 150-250° C., more preferably 200-250° C.

Preferably, the stirring speed is 200-300 r/min, more preferably 200-250 r/min.

Preferably, the reaction time is 2.5-3 h, more preferably 3 h.

Preferably, the preparation method of the catalyst is as follows: a supported nickel-based catalyst is prepared by an equal volume impregnation method, which is reduced in a hydrogen atmosphere to obtain a black powdery solid, i.e., the catalyst.

Preferably, the preparation method of the catalyst specifically comprises the following steps:
1) the supported nickel-based catalyst is prepared by an equal volume impregnation method as follows: nickel nitrate is added to distilled water and stirred for 15-25 min, then a catalyst carrier is added and stirred for 15-25 min, which is dried at 85-95° C. and taken out to obtain solid A;
2) under a hydrogen atmosphere, the solid A obtained in step 1) is reduced at 550-650° C. for 2.5-3.5 hours to obtain a black powdery solid B, i.e., the catalyst;

Preferably, the Ni content in the supported nickel-based catalyst is 15-20 wt %.

Preferably, the catalyst carrier is a $CeO_2$ carrier or $Al_2O_3$ carrier.

Preferably, the preparation method of $CeO_2$ carrier is as follows: cerium nitrate is baked at 550-650° C. for 1.5-2.5 hours to obtain a $CeO_2$ carrier.

Preferably, the biogas slurry and the catalyst are added to the reactor for reaction.

Preferably, the reactor is a micro-reactor equipped with means for heating, pressurizing and stirring.

Preferably, the cooling step in the cooling and collecting gas is realized by an ice bath cooling method.

In an exemplary embodiment, a method for preparing biochar and hydrogen by utilizing anaerobic fermentation byproducts in the present disclosure is as follows: the naturally air-dried straw is coarsely pulverized into 2-3 cm; the straw, seeding sludge at a mass ratio of seeding sludge to straw of (25-30):1, and distilled water at a mass ratio of distilled water to straw of (10-20):1 are uniformly mixed, and poured into a fermentation tank, and then nitrogen gas is purged to ensure anaerobic conditions; the fermentation tank is placed in a room temperature environment for 7-14 days, and regularly stirred; the fermented mixed materials are sieved and washed to recover the fermented straw; sieve residue is precipitated and separated by centrifugation, and the biogas slurry is collected; the straw powders are obtained by drying and pulverization, and placed in a pyrolytic furnace for carbonization to obtain the biochar; 100 mL of the biogas slurry is placed in a reactor, and the reactor is sealed after adding the catalyst and a magnetic rotor; nitrogen gas is introduced to exhaust the air and the pressure is adjusted to 2.5-3.0 MPa, the temperature is 200-250° C., and the stirring speed reaches 200-300 r/min; after reacting for 3 hours, the reactor is placed in an ice bath to cool to the room temperature, and the non-condensable gas obtained at the gas outlet is a gas phase product containing hydrogen.

The specific surface area of the biochar obtained from the biomass after the anaerobic fermentation treatment of the present disclosure reaches 240-288 $m^2/g$. Compared with the initial straw, the specific surface area of biochar is increased by 31-79 $m^2/g$, effectively improving the performance of the biochar. The prepared biochar can be directly used in the fields of soil fertility improvement, carbon sink increase and emission reduction, and environmental pollution restoration.

The seeding sludge of the present disclosure is discharged sludge from the anaerobic fermentation tank under normal operation.

The pyrolytic carbonization device of the present disclosure includes but is not limited to a high-temperature tube furnace, and may be other high-temperature devices that can realize pyrolysis.

The high-temperature tube furnace of the present disclosure has a carbonization temperature of 800° C. However, this temperature can be adjusted during the actual application, as long as the pyrolytic carbonization of straw can be realized.

The pyrolytic carbonization time of the present disclosure is 60 min. This time can be appropriately adjusted according to actual requirements, and can be based on no release of combustible components in the pyrolytic gas to ensure complete pyrolysis.

The biogas slurry used in the present disclosure includes, but is not limited to, straw and liquid phase byproducts obtained by anaerobic fermentation of sludge.

The supported nickel-based catalyst carrier for hydrogen production from biogas slurry in the present disclosure includes but is not limited to $CeO_2$ or $Al_2O_3$. Any carrier with high specific surface area, high thermal stability, or the like can be adopted as the catalyst carrier used in the present disclosure, for example, molecular sieve, activated carbon carrier, etc.

The loading amount of the active component Ni in the supported nickel-based catalyst for hydrogen production from biogas slurry of the present disclosure is in the range of 15-20 wt %. If the loading amount is too low, the number of the metal active sites is insufficient, and thus the reaction rate is low. If the loading amount is too high, it will lead to metal agglomeration, and thus the catalytic activity is low. The catalyst dosage is 2-5 g/L; if the dosage is too low, it is not enough to exert the catalytic effect, and if the dosage is too high, it will increase the cost.

The reactor for hydrogen production from biogas slurry of the present disclosure is a micro-reactor equipped with means for heating, pressurizing and stirring.

The reaction pressure for hydrogen production from biogas slurry in the present disclosure is in the range of 2.5-3.0 MPa. When the pressure is below 2.5 MPa, the saturated vapor pressure of the biogas slurry will be easily reached to gasify the raw material. When the pressure is above 3.0 MPa, side reactions increase, which is detrimental to $H_2$ generation.

The catalytic reaction temperature for hydrogen production from biogas slurry in the present disclosure is in the range of 200-250° C. When the temperature is below 200° C., the organic nitrogen in the biogas slurry is easily reacted with water to produce ammonia. When the temperature is above 250° C., the water-gas shift reaction is increased, the hydrogen content and selectivity are decreased, CO2 content is increased, and energy consumption is increased.

In another exemplary embodiment, a method for preparing biochar and hydrogen by utilizing anaerobic fermentation byproducts in the present disclosure comprises the following steps:

1) Coarse pulverization of straw: the naturally air-dried straw is coarsely pulverized, and the straw with a length of about 2-3 cm is used for subsequent treatment;
2) Anaerobic fermentation treatment: the straw pulverized in step 1) and seeding sludge at a mass ratio of seeding sludge to straw of (25-30):1 are uniformly mixed and poured into a fermentation tank, and distilled water at a mass ratio of distilled water to straw of (10-20):1 is added, and the mixed materials are stirred well. A nitrogen pipe is submerged into the bottom of the fermentation tank to purge for 3-5 min to ensure an anaerobic environment. There is a biogas outlet on the top of the fermentation tank. An exit pipe is submerged into water to prevent the air from flowing back into the fermentation tank. The fermentation tank is placed in an environment of normal temperature 20-25° C. for 7-14 days, and the fermented materials are stirred approximately every 12 hours to prevent slagging and floating;
3) Recovery of fermented straw: the mixed materials after the fermentation treatment in step 2) are screened, and the oversized materials are rinsed repeatedly with tap water until the washed solution is transparent and colorless to obtain the pretreated straw;
4) Collection of fermented biogas slurry: the undersized materials of the mixed materials after the fermentation treatment in step 3) are precipitated and centrifuged. The centrifuged supernatant is obtained as the biogas slurry;
5) Drying and pulverization of straw: the washed straw is placed in an oven at 55-60° C. for 48 hours, then pulverized and sieved to obtain the straw with 40-80 mesh for use;
6) Carbonization of straw: the straw pulverized and sieved in step 4) is placed in a pyrolytic furnace for carbonization, and the reaction is performed until no combustible components are released in the pyrolytic gas, and naturally cooled to the room temperature to obtain the straw biochar;
7) Preparation of catalyst for hydrogen production from biogas slurry: the supported nickel-based catalyst is prepared by an equal volume impregnation method as follows: nickel nitrate is added to distilled water and stirred for 15-25 min, then a catalyst carrier is added and stirred for 15-25 min, which is dried at 85-95° C. and taken out to obtain solid A;
8) Hydrogen reduction of the catalyst for hydrogen production from biogas slurry: under a hydrogen atmosphere, the solid A obtained in step 7) is reduced at 550-650° C. for 2.5-3.5 hours to obtain a black powdery solid B, i.e., the catalyst;

wherein the Ni amount is 15-20 wt %, and the carrier may be $CeO_2$ and $Al_2O_3$, etc.; and a black powdery catalyst is obtained after reduction under a hydrogen atmosphere.

9) Catalytic and pressurized hydrogen production from biogas slurry: the reactor is sealed after adding the biogas slurry, the catalyst in step 7) and a magnetic rotor; then nitrogen is introduced to exhaust the air, and the pressure is adjusted to 2.5-3.0 MPa, the reaction temperature is 200-250° C., the stirring speed is 200-300 r/min, and the reaction time is 3 hours;

10) Product collection of hydrogen from biogas slurry: after stopping the heating and stirring, the reactor is placed in an ice bath to cool to room temperature, and the non-condensable gas obtained at the gas outlet is the gas phase products containing hydrogen.

EXAMPLES

The technical solutions of the present disclosure will be further explained herein below through specific examples with reference to the accompanying drawings. It should be noted that the following specific examples are merely illustrative, and the protection scope of the present disclosure is not limited thereto.

The chemical reagents and raw materials used in the following examples are all commercially available or self-made by well-known preparation methods.

Example 1

Figure 1:
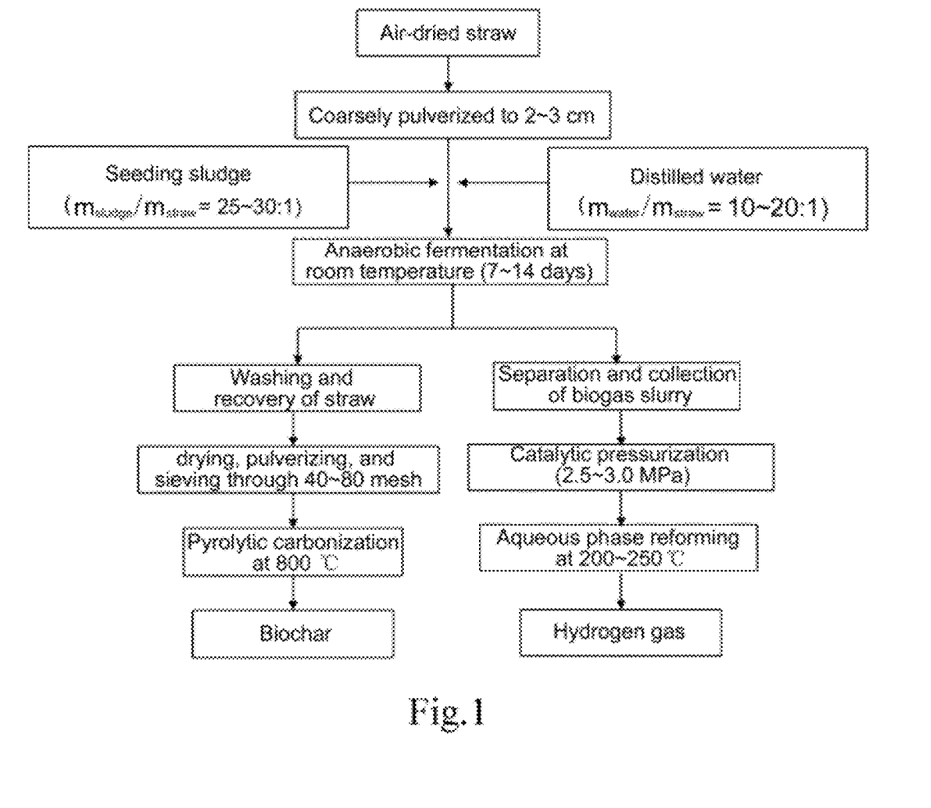
FIG. 1 is a process flow chart of an example of the present disclosure.

A method for preparing biochar and hydrogen by utilizing anaerobic fermentation byproducts adopted the process flow as shown in FIG. 1.

Figure 5:
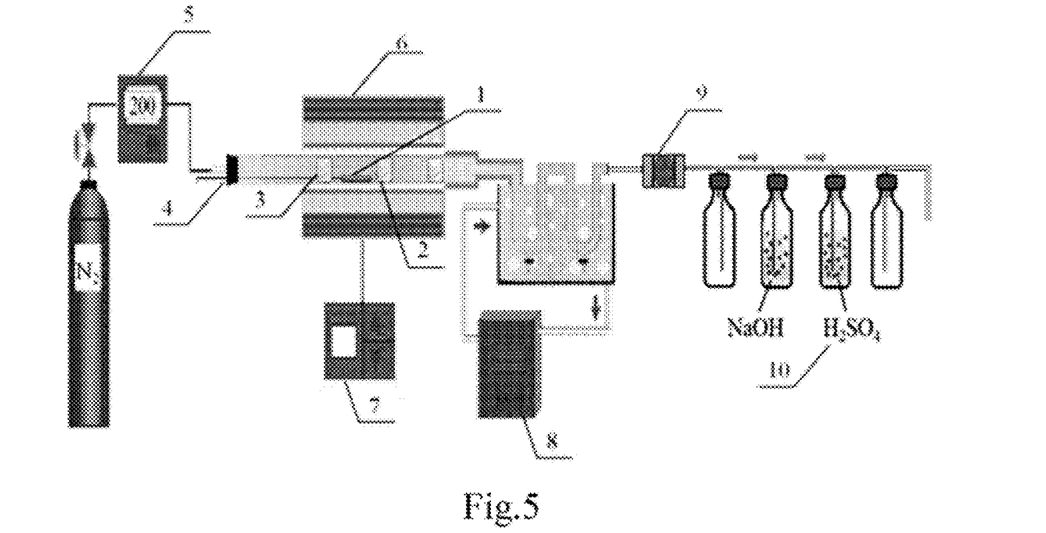
FIG. 5 is a flow chart of the high-temperature tube furnace pyrolytic device in Example 1 of the present disclosure.
Figure 6:
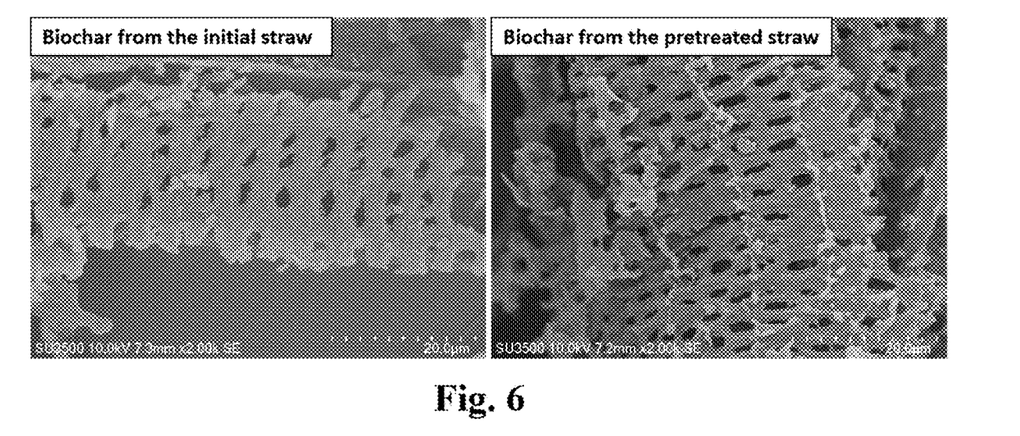
FIG. 6 is a scanning electron micrograph of the straw biochar before and after the anaerobic fermentation treatment in Example 1 of the present disclosure.
Figure 7:
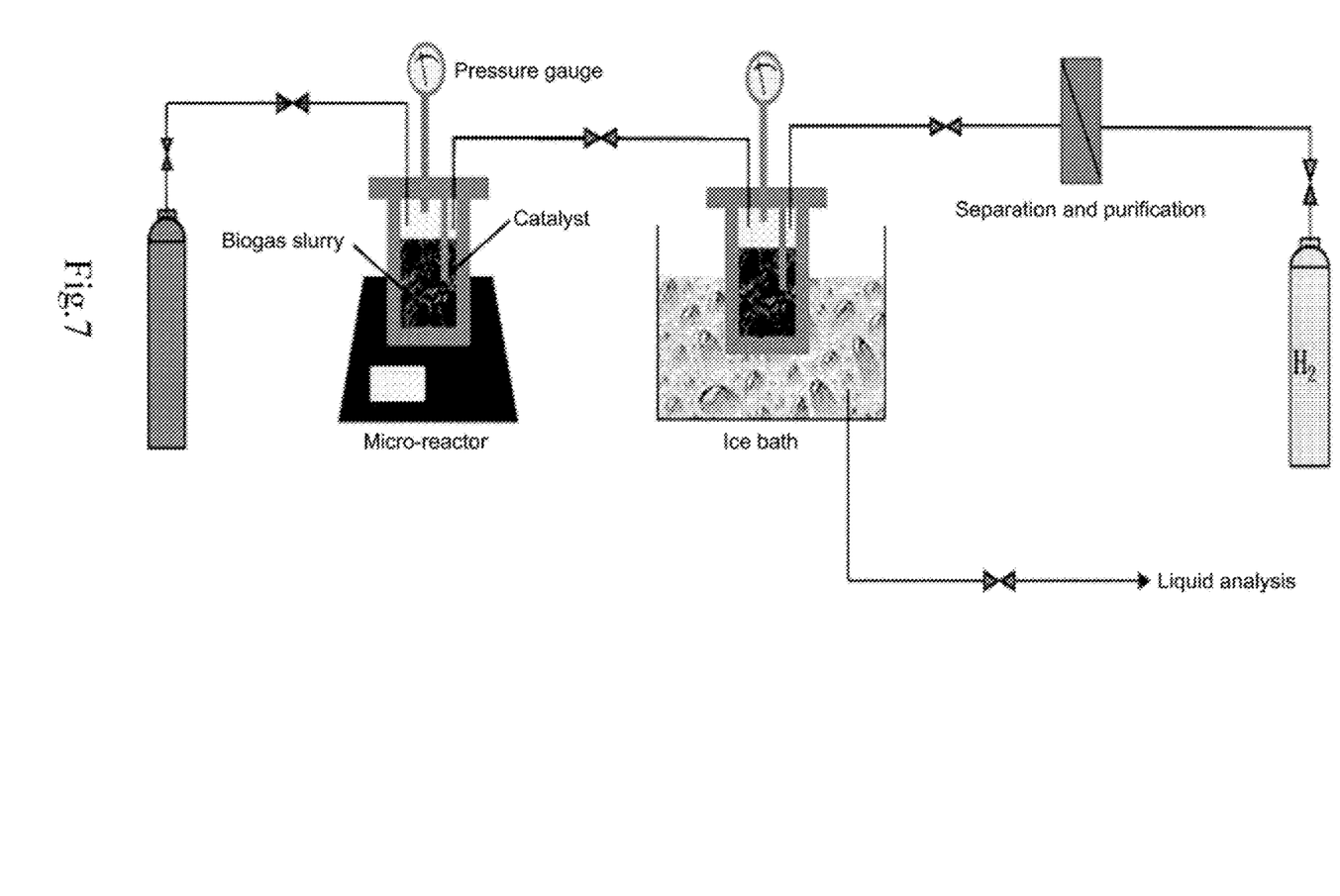
FIG. 7 is a flow chart of biogas slurry derived from anaerobic fermentation to produce hydrogen in an example of the present disclosure.

1) Coarse pulverization of straw: 500 g of the naturally air-dried corn straw was coarsely pulverized, and the straw with a length of about 2 cm was taken for use;

2) Anaerobic fermentation treatment: 15 kg of the seeding sludge (the mass ratio of seeding sludge to straw being 30:1) and the coarsely pulverized straw were uniformly mixed and poured into a fermentation tank, and then 10 kg of the distilled water (the mass ratio of distilled water to straw mass being 20:1) was added, and the mixed materials were stirred well; a nitrogen gas pipe was submerged into the bottom of the fermentation tank to purge for 3 min to ensure an anaerobic environment; and there was a biogas outlet on the top of the fermentation tank, and an exit pipe was submerged into water to prevent the air from flowing back into the fermentation tank. The fermentation tank was placed in an environment of 25° C. for 14 days, and the fermented materials were stirred every 12 hours to prevent slagging and floating;

3) Recovery of fermented straw: the mixed materials after the fermentation pretreatment in step 2) were screened, and the oversize materials were rinsed repeatedly with tap water until the washed solution was transparent and colorless to obtain the treated straw;

4) Collection of fermented biogas slurry: the undersized materials of the mixed materials after the fermentation treatment in step 3) were precipitated and centrifuged. The centrifuged supernatant was obtained as the biogas slurry;

5) Drying and pulverization of straw: the washed straw was placed in an oven at 60° C. for drying, and the dried straw was pulverized and sieved to obtain the straw with 40-80 mesh for characterization and carbonization; the Fourier transform infrared spectra, the X-ray diffraction pattern, and the scanning electron micrograph of the pretreated straw were shown in FIG. 2, FIG. 3, and FIG. 4, respectively. As shown in FIG. 2, the absorption strength of cellulose and hemicellulose was weakened at 1723 $cm^{-1}$, 1379 $cm^{-1}$, 1161 $cm^{-1}$, and 899 $cm^{-1}$, and the lignin stretching vibration peaks were enhanced at 1601 $cm^{-1}$, 1515 $cm^{-1}$, and 1247 $cm^{-1}$, indicating that the mild anaerobic fermentation pretreatment improved the organic composition of the straw, reduced the contents of cellulose and hemicellulose, and enriched the lignin. It demonstrated that the anaerobic fermentation pretreatment improved the organic composition of the biomass, reducing the generation of volatile products (tar) from the source during the carbonization, and reduced the risk of biochar pore blockage by tar; as shown in FIG. 3, the diffraction intensity representing the ordered structure of the straw at $2\theta \approx 22°$-$23°$ became weaker, the diffraction peak became broader, and the randomness of the straw structure was enhanced after pretreatment; as shown in FIG. 4, the straw structure was loose and the pores were obvious after pretreatment, which helped to strengthen the mass and heat transfer effects during the carbonization, promoted the rapid escape of volatiles, and left abundant pores, so as to produce biochar with high specific surface area;

6) Carbonization of straw: the high-temperature tube furnace in FIG. 5 was used for the pyrolytic carbonization of the straw. The straw pulverized and sieved in step 4) was placed in the quartz crucible 1, and the crucible was placed at one end of the high-temperature tube furnace 6. The first high-temperature resistant ceramic pipe plug 2 and the second high-temperature resistant ceramic pipe plug 3 were respectively placed at both ends of the crucible, wherein the first high-temperature resistant ceramic pipe plug 2 was used to isolate the heating zone of the high-temperature tube furnace 6, and the second high-temperature resistant ceramic pipe plug 3 was connected with the stainless steel pushrod 4. The high-temperature tube furnace 6 was closed and initiated, the mass flowmeter 5 was used to control the nitrogen flow rate to 200 mL/min, and the temperature control system 7 was adjusted such that the furnace body of the high-temperature tube furnace 6 was heated to the required pyrolytic temperature of 800° C. in a nitrogen atmosphere. The stainless steel pushrod 4 was used to push the second high-temperature resistant ceramic pipe plug 3 and the crucible to the heating zone of the high-temperature tube furnace 6, followed by constant temperature pyrolysis for 60 min and natural cooling to the room temperature to obtain the biochar. The pyrolytic gas is flowed through the condenser 8, filter 9, and pyrolytic gas purification system 10, and then was collected, burned, and discharged. The scanning electron micrograph of the biochar was shown in FIG. 6. It can be seen that the pore structure of the straw biochar was more abundant after the mild fermentation pretreatment. The specific surface area of the prepared biochar was tested with an automatic specific surface area analyzer, and the specific values were shown in Table 1;

7) Preparation of catalyst for hydrogen production from biogas slurry and hydrogen reduction: a $Ni/Al_2O_3$ catalyst with a Ni loading amount of 15 wt % was prepared by an equal volume impregnation method, which was reduced under a hydrogen atmosphere to obtain a black powdery catalyst;

8) Catalytic and pressurized hydrogen production from biogas slurry: 0.2 g of catalyst and 100 mL of biogas slurry were placed in the reactor, and then the reactor was sealed; nitrogen was introduced to exhaust the air and the pressure was adjusted to 2.5 MPa, the temperature was heated to 250° C., the stirring speed was 250 r/min, and the reaction time was 3 hours;

9) Products collection of hydrogen from biogas slurry: after stopping the heating and stirring, the reactor was placed in an ice bath to cool to the room temperature, and the non-condensable gas obtained at the gas outlet was the gas phase products containing hydrogen. The composition and the contents of the gas product were shown in Table 2.

Example 2

This example used the same raw materials and method as those in Example 1, except that the nickel-based catalyst carrier in the hydrogen production from biogas slurry was $CeO_2$. The test data of the specific surface area for the biochar from the biogas residue as anaerobic fermentation byproducts were shown in Table 1, and the composition and the contents of the gas product of the hydrogen production from biogas slurry were shown in Table 2.

Example 3

This example used the same raw materials and method as those in Example 1, except that the catalyst dosage in the hydrogen production from biogas slurry was 0.5 g, and the reactor was heated to 200° C. The test data of the specific surface area for the biochar from the biogas residue as anaerobic fermentation byproducts were shown in Table 1, and the composition and the contents of the gas product of the hydrogen production from biogas slurry were shown in Table 2.

Example 4

This example used the same raw materials and method as those in Example 1, except that the catalyst dosage in the hydrogen gas production from biogas slurry was 0.5 g, and the reaction pressure was 2.8 MPa. The test data of the specific surface area for the biochar from the biogas residue as anaerobic fermentation byproducts were shown in Table 1, and the composition and the contents of the gas product of the hydrogen production from biogas slurry were shown in Table 2.

Example 5

This example used the same raw materials and method as those in Example 1, except that the catalyst dosage in the hydrogen production from biogas slurry was 0.5 g, and the reaction pressure of the reactor was 3.0 MPa. The test data of the specific surface area for the biochar from the biogas residue as anaerobic fermentation byproducts were shown in Table 1, and the composition and the contents of the gas product of the hydrogen production from biogas slurry were shown in Table 2.

Example 6

This example used the same raw materials and method as those in Example 1, except that the nickel-based catalyst carrier in the hydrogen gas production from biogas slurry was $CeO_2$, the catalyst dosage was 0.5 g, and the reactor was heated to 200° C. The test data of the specific surface area for the biochar from the biogas residue as anaerobic fermentation byproducts were shown in Table 1, and the composition and the contents of the gas product of the hydrogen production from biogas slurry were shown in Table 2.

Example 7

This example used the same raw materials and method as those in Example 1, except that the nickel-based catalyst carrier in the hydrogen gas production from biogas slurry was $CeO_2$, the catalyst dosage was 0.5 g, the reactor was heated to 225° C., and the reaction pressure of the reactor was 2.8 MPa. The test data of the specific surface area for the biochar from the biogas residue as anaerobic fermentation byproducts were shown in Table 1, and the composition and the contents of the gas product of the hydrogen production from biogas slurry were shown in Table 2.

Example 8

This example used the same raw materials and method as those in Example 1, except that the nickel-based catalyst carrier in the hydrogen gas production from biogas slurry was $CeO_2$, the catalyst dosage was 0.5 g, and the reaction pressure of the reactor was 3.0 MPa. The test data of the specific surface area for the biochar from the biogas residue as anaerobic fermentation byproducts were shown in Table 1, and the composition and the contents of the gas product of the hydrogen production from biogas slurry were shown in Table 2.

Example 9

This example used the same raw materials and method as those in Example 1, except that the seeding sludge had a mass of 13.75 kg (the mass ratio of seeding sludge to straw being 27.5:1), the distilled water had a mass of 7.5 kg (the mass ratio of distilled water to straw being 15:1), and the fermentation pretreatment period was 10 days.

The test data of the specific surface area for the biochar from the biogas residue as anaerobic fermentation byproducts were shown in Table 1.

Example 10

This example used the same raw materials and method as those in Example 1, except that the seeding sludge had a mass of 12.5 kg (the mass ratio of seeding sludge to straw being 25:1), the distilled water had a mass of 5 kg (the mass ratio of distilled water to straw being 10:1), and the fermentation pretreatment period was 7 days.

The test data of the specific surface area for the biochar from the biogas residue as anaerobic fermentation byproducts were shown in Table 1.

Table 1 summarizes the data for the carbonization from biogas residue as anaerobic fermentation byproducts in the Examples.

| | Operating conditions | | | Biochar properties |
|---|---|---|---|---|
| Item | Mass ratio of seeding sludge to straw | Mass ratio of distilled water to straw | Period/days | Specific surface area ($m^2/g$) |
| Blank | none | none | none | 209 |
| Examples 1-8 | 30 | 20 | 14 | 288 |
| Example 9 | 27.5 | 15 | 10 | 255 |
| Example 10 | 25 | 10 | 7 | 240 |

Table 2 summarizes the data for the hydrogen production from biogas slurry as anaerobic fermentation byproducts in the Examples.

| | | | Operating conditions | | | | Gas volume ratio | | |
|---|---|---|---|---|---|---|---|---|---|
| Example No. | Catalyst Type | Catalyst amount | Temperature/ °C. | Pressure/ MPa | Stirring rate/r/min | Reaction time/h | $H_2$/% | $CO_2$/% | $NH_3$/% |
| 1 | Ni/$Al_2O_3$ | 0.2 | 250 | 2.5 | 250 | 3 | 0 | 8.934 | 91.06 |
| 2 | Ni/$CeO_2$ | 0.2 | 250 | 2.5 | 250 | 3 | 0.97 | 0.44 | 98.59 |
| 3 | Ni/$Al_2O_3$ | 0.5 | 200 | 2.5 | 250 | 3 | 0 | 22.53 | 77.47 |
| 4 | Ni/$Al_2O_3$ | 0.5 | 225 | 2.8 | 250 | 3 | 6.23 | 26.22 | 67.55 |
| 5 | Ni/$Al_2O_3$ | 0.5 | 250 | 3.0 | 250 | 3 | 5.64 | 19.44 | 74.92 |
| 6 | Ni/$CeO_2$ | 0.5 | 200 | 2.5 | 250 | 3 | 21.53 | 35.03 | 43.44 |
| 7 | Ni/$CeO_2$ | 0.5 | 225 | 2.8 | 250 | 3 | 35.44 | 27.72 | 36.84 |
| 8 | Ni/$CeO_2$ | 0.5 | 250 | 3.0 | 250 | 3 | 9.11 | 25.40 | 65.49 |

The present disclosure proposes a method for preparing biochar and hydrogen from anaerobic fermentation byproducts, which is simple in operation, low in cost and environmentally friendly. Those skilled in the art can realize the present invention by appropriately changing the raw material proportions, the fermentation period during the fermentation pretreatment, the reaction temperature and the reaction pressure in hydrogen production from biogas slurry in accordance with the disclosure herein. Therefore, the method for preparing biochar and hydrogen by utilizing anaerobic fermentation byproducts in the present disclosure has at least one of the following advantages over the prior art:

1. The present disclosure proposes the method and use for preparing biochar from the biogas residue as anaerobic fermentation solid byproducts and for preparing hydrogen from liquid byproducts, provides a new route for resource recycling and disposal of anaerobic fermentation byproducts, and provides technical references for the preparation of biochar with high specific surface area from biomass and hydrogen production from biogas slurry;

2. The present disclosure proposes to couple the anaerobic fermentation process with the carbonization process. The anaerobic fermentation can effectively improve the composition proportion of biomass lignocellulose and breakdown the chimeric structure inside the biomass, reducing the risk of blocking the pores of biochar by the tar from the source during carbonization, and enhancing the mass and heat transfer process during carbonization, significantly improving the specific surface area of the biochar obtained from carbonization. The specific surface area of the biochar prepared by this method reaches 240-288 $m^2/g$, significantly higher than the specific surface area (209 $m^2/g$) of the biochar prepared by the initial biomass; the pore structure of the biochar obtained after pretreatment is more abundant, improving the use performance to a certain extent. It can be used in the fields of soil fertility improvement, carbon sink increase and emission reduction, and environmental pollution restoration, with a great potential;

3. The present disclosure provides a method for preparing hydrogen by aqueous phase reforming of renewable biogas slurry. The method omits the vaporization step of raw materials, and directly produces hydrogen in a one-step reaction under relatively mild reaction conditions (150-250° C., 1.5-5.0 MPa), while minimizing the influence of side reactions that are easily occurred under high temperature conditions; under the optimal implementation conditions, the proportion of hydrogen in the detectable components is 35% or more; the hydrogen produced can enrich the forms of gas in the biogas industry chains and enhance the values of gas product; and the hydrogen can be used for heating or power generation on-site;

4. The present disclosure is simple in operation, low in cost and environmentally friendly, and broadens the routes and methods for the disposal of biogas residue and biogas slurry as anaerobic fermentation byproducts.

The specific examples described above further illustrate the objectives, technical solutions, and beneficial effects of the present disclosure in detail. It should be understood that the above descriptions are merely specific examples of the present disclosure and are not intended to limit the present disclosure. Any modifications, equivalent replacements, improvements, and the like within the spirit and principle of the present disclosure shall be included in the protection scope of the present disclosure.

The invention claimed is:

1. A method for preparing biochar and hydrogen by utilizing anaerobic fermentation byproducts, the method comprising:
   mixing first straw, seeding sludge, and distilled water for anaerobic fermentation to obtain a fermented mixed product;
   separating fermented straw from the fermented mixed product to obtain second straw;

separating and recovering a biogas slurry from the fermented mixed product;
carbonizing the obtained second straw to obtain the biochar; and
collecting gas after a pressurized catalytic reaction of the obtained biogas slurry.

2. The method according to claim 1, wherein:
the seeding sludge and the first straw have a mass ratio of (25-30):1;
the distilled water and the first straw have a mass ratio of (10-20):1;
the first straw has a length of 2-3 cm;
the first straw is an air-dried straw;
the second straw is washed and dried before the carbonization step;
the second straw has mesh number of 40-80 mesh.

3. The method according to claim 1, wherein:
the anaerobic fermentation is realized in an anaerobic fermentation tank;
the seeding sludge is discharged sludge from an anaerobic fermentation tank;
the anaerobic fermentation is realized at a fermentation temperature of 20-25° C.; the anaerobic fermentation is realized in a fermentation time of 7-14 days; and the first straw, the seeding sludge and the distilled water are stirred every 10-14 hours;
during the anaerobic fermentation, an anaerobic environment is realized by introducing inert gas comprising nitrogen.

4. The method according to claim 1, wherein:
the carbonization step is realized in a pyrolytic carbonization device;
the pyrolytic carbonization device comprises a high-temperature tube furnace;
in the carbonization step, the high-temperature tube furnace has a carbonization temperature of 750-850° C. and a pyrolytic carbonization time is 50-70 min.

5. The method according to claim 1, wherein the step of collecting gas after a pressurized catalytic reaction of the obtained biogas slurry comprises, after adding a catalyst to the biogas slurry, reacting under a pressurized condition, and then cooling and collecting gas.

6. The method according to claim 5, wherein:
the catalyst has a concentration of 2-5 g/L;
the reaction pressure is 1.5-5.0 MPa.

7. The method according to claim 6, wherein the reaction pressure is 2.5-3.0 MPa.

8. The method according to claim 5, wherein:
the pressurized catalytic reaction is realized at a reaction temperature of 150-250° C.;
the pressurized catalytic reaction is realized in a reaction time of 2.5-3 hours.

9. The method according to claim 8, wherein:
the reaction temperature is 200-250° C.;
the reaction time is 3 hours.

10. The method according to claim 5, wherein the pressurized catalytic reaction is realized with a stirring speed of 200-300 r/m in.

11. The method according to claim 10, wherein the stirring speed is 200-250 r/min.

12. The method according to claim 5, wherein a method for catalyst preparation comprises: a supported nickel-based catalyst is prepared by an equal volume impregnation method, which is reduced in a hydrogen gas atmosphere to obtain a black powdery solid comprising the catalyst.

13. The method according to claim 12, wherein the method for catalyst preparation comprises:
1) the supported nickel-based catalyst is prepared by an equal volume impregnation method: nickel nitrate is added to distilled water and stirred for 15-25 min, then a catalyst carrier is added and stirred for 15-25 min, and dried at 85-95° C. and taken out to obtain a solid A;
2) under a hydrogen gas atmosphere, the solid A obtained in step 1) is reduced at 550-650° C. for 2.5-3.5 hours to obtain a black powdery solid B comprising the catalyst,
wherein the Ni content in the supported nickel-based catalyst is 15-20 wt %.

14. The method according to claim 13, wherein:
the catalyst carrier is a $CeO_2$ carrier or $Al_2O_3$ carrier, wherein the $CeO_2$ carrier is prepared by baking cerium nitrate 550-650° C. for 1.5-2.5 hours to obtain the $CeO_2$ carrier;
the biogas slurry and the catalyst are added to a reactor for reaction, the reactor comprising a micro-reactor equipped with means for heating, pressurizing and stirring;
the cooling step in the cooling and collecting gas is realized by an ice bath cooling method.

15. A biochar prepared by the method according to claim 1, wherein the biochar has a specific surface area of 240-288 $m^2$/g.

* * * * *